(12) United States Patent
Voudouris (10) Patent No.: US 10,105,193 B2
(45) Date of Patent: Oct. 23, 2018

(54) ORTHODONTIC BRACKET

(75) Inventor: John Voudouris, Toronto (CA)

(73) Assignee: Orthoarm, Inc., Toronto (CA)

( * ) Notice: Subject to any disclaimer, the term of this patent is extended or adjusted under 35 U.S.C. 154(b) by 275 days.

(21) Appl. No.: 13/984,295

(22) PCT Filed: Feb. 10, 2012

(86) PCT No.: PCT/CA2012/050077
§ 371 (c)(1),
(2), (4) Date: Oct. 7, 2013

(87) PCT Pub. No.: WO2012/106825
PCT Pub. Date: Aug. 12, 2012

(65) Prior Publication Data
US 2014/0023981 A1 Jan. 23, 2014

Related U.S. Application Data

(60) Provisional application No. 61/442,047, filed on Feb. 11, 2011, provisional application No. 61/442,053, filed on Feb. 11, 2011.

(51) Int. Cl.
*A61C 7/28* (2006.01)
(52) U.S. Cl.
CPC .............. *A61C 7/287* (2013.01); *A61C 7/285* (2013.01)
(58) Field of Classification Search
CPC ........... A61C 7/28; A61C 7/287; A61C 8/285; A61C 7/285
See application file for complete search history.

(56) References Cited

U.S. PATENT DOCUMENTS 4,712,999 A 12/1987 Rosenberg
5,474,445 A 12/1995 Voudouris
(Continued)

FOREIGN PATENT DOCUMENTS

WO WO2005096984 10/2005

*Primary Examiner* — Edward Moran
(74) *Attorney, Agent, or Firm* — McMillan LLP (57) ABSTRACT

An orthodontic bracket for attaching an archwire to a tooth including a body including a bonding base for attachment to the tooth, the body having an occlusal-gingivally extending opening, a lingual vertical slot, a pair of laterally spaced gingival tie wings and a pair of laterally spaced occlusal tie wings, the gingival and occlusal tie wings projecting from a labial surface of the body. An archwire slot is provided extending mesiodistally across the body and between the gingival and occlusal tie wings at opposed medial and distal sides of the body to accommodate the archwire. A locking shutter including at least one resilient arm member at one end and a retaining portion at another end is provided such that the locking shutter moveable between an open position in which placement and removal of the archwire is facilitated and a closed position in which placement and removal of the archwire is inhibited. There is further provided a retaining groove formed in an occlusal wall of the gingival tie wings for releasably retaining a retaining portion of the locking shutter in the closed position and, at least one blocker for preventing movement of the archwire out of the archwire slot and into the retaining groove. In addition, a broader locking shutter is possible that prevents a sharp bend in the archwire to prevent notching or bonding of the archwire during early tooth movement and sliding of teeth during mid-term treatment tooth movement.

6 Claims, 9 Drawing Sheets

(56) References Cited

U.S. PATENT DOCUMENTS

| | | |
|---|---|---|
| 5,630,715 A | 5/1997 | Voudouris |
| 5,857,850 A | 1/1999 | Voudouris |
| 5,906,486 A * | 5/1999 | Hanson .................. A61C 7/287 433/10 |
| 5,908,293 A | 6/1999 | Voudouris |
| 5,913,680 A | 6/1999 | Voudouris |
| 6,168,428 B1 | 1/2001 | Voudouris |
| 6,257,883 B1 * | 7/2001 | Voudouris ............... A61C 7/02 433/11 |
| 6,302,688 B1 | 10/2001 | Jordan et al. |
| 6,368,105 B1 | 4/2002 | Voudouris |
| 6,554,612 B2 | 4/2003 | Georgakis et al. |
| 6,582,226 B2 | 6/2003 | Jordan et al. |
| 6,843,651 B2 | 1/2005 | Orikasa |
| 6,939,133 B2 | 9/2005 | Voudouris |
| 6,984,127 B2 | 1/2006 | Lai |
| 7,014,460 B2 | 3/2006 | Lai et al. |
| 7,063,531 B2 | 6/2006 | Maijer |
| 7,186,114 B2 | 3/2007 | Navarro |
| 7,192,274 B2 | 3/2007 | Stadtmiller et al. |
| 7,214,057 B2 | 5/2007 | Voudouris |
| 7,442,039 B2 | 10/2008 | Opin et al. |
| 7,585,171 B2 | 9/2009 | Hagelganz et al. |
| 7,674,110 B2 | 3/2010 | Oda |
| 7,780,443 B2 | 8/2010 | Hagelganz et al. |
| 7,878,802 B2 | 2/2011 | Hagelganz et al. |
| 7,909,603 B2 | 3/2011 | Oda |
| 2004/0157186 A1 * | 8/2004 | Abels ..................... A61C 7/285 433/10 |
| 2005/0239012 A1 * | 10/2005 | Bathen .................. A61C 7/287 433/10 |
| 2006/0110699 A1 * | 5/2006 | Forster .................. A61C 7/287 433/11 |
| 2006/0228662 A1 | 10/2006 | Lokar |
| 2006/0228664 A1 | 10/2006 | Castner |
| 2006/0269895 A1 | 11/2006 | Voudouris |
| 2007/0243497 A1 * | 10/2007 | Voudouris ...................... 433/10 |
| 2009/0170049 A1 | 7/2009 | Heiser |
| 2010/0311004 A1 | 12/2010 | Voudouris |
| 2011/0076633 A1 | 3/2011 | Bryant |
| 2013/0236847 A1 | 9/2013 | Shin |

* cited by examiner

ORTHODONTIC BRACKET

RELATED APPLICATIONS

This application claims priority to U.S. Provisional Application No. 61/442,047 filed Feb. 11, 2011 and to U.S. Provisional Application No. 61/442,053 filed Feb. 11, 2011. The contents of both of these are herein expressly incorporated by reference.

FIELD OF THE INVENTION

The present invention relates to the field of orthodontic brackets, and more particularly to an orthodontic bracket having a means for restricting undesired movement of an archwire.

BACKGROUND OF THE INVENTION

Orthodontic treatment is effected by fixing small appliances often referred to as orthodontic brackets to a patient's teeth in an appropriate manner so as to correct malaligned teeth by applying an external force thereto through an archwire extending between the generally fixed orthodontic brackets. As to the structure of these orthodontic brackets, they are constructed of a body having small slots and are adhered directly on the labial or lingual sides of the teeth or welded to metal bands attached to the teeth by cementing or by some other method, as is generally known in the art.

As the form of use of the orthodontic bracket constructed as described above, a flexible archwire, which is curved so as to conform to a dental arch, is placed in an archwire slot in the bracket, and the tooth can be shifted over time by the restoring force of the archwire so that the teeth become well aligned. With the orthodontic bracket, a force can be applied to the tooth in a desired direction to correct the direction in which the tooth is shifted, rotated, tipped or torqued. This is effected by the three-dimensional inclination of the slot formed in the bracket body or by the desired bending of the archwire.

The conventional orthodontic bracket has tie wings, and a ligature wire or an elastomeric ligature ring is hooked on the tie wings so as to positively hold the archwire to prevent the archwire from coming out of the slot in the bracket. The dentition that should be treated is of malocclusion, in which the archwires are greatly deformed when engaged. Orthodontic treatment is accomplished by transmitting the restoring force of the archwires through brackets to the tooth roots. Generally, in an early period of the treatment, a thin, highly flexible round archwire is used, and an operation is required to loosen the ligature wire after ligating it such that the round wire freely slides within the slot (on a very low frictional basis). As treatment progresses, a thicker wire, a square ro rectangular wire, and a more highly rigid wire come to be used. When the alignment is nearly completed, they are held for a while to prevent relapse. At this time, there are cases where the tooth is strongly fastened by a ligature wire so that it practically does not shift.

In the orthodontic treatment as described above, different archwires of many varieties are used in succession during the course of the treatment. During patient visits to the clinic, it is necessary to remove the ligature wire and adjust the bend of the archwire or replace it. This operation requires much chair time and imparts discomfort to the patients.

The various problems due to the use of this type of a ligature wire can be overcome to some extent by using a lock-type orthodontic bracket. Namely, this lock-type orthodontic bracket has a structure which does not require the tie wire for ligation, and has a locking member incorporated into the bracket and capable of shifting for opening or closing the slot in the bracket. As the locking members, there are, for example, rotating-type and sliding-type locking members. Since the locking members are capable of shifting in open and/or closed positions whereby the retention of the archwire in the slot or disengagement of the archwire from the slot can be easily affected. One example of an orthodontic bracket as described above is shown in U.S. Pat. No. 6,168,428 issued Jan. 2, 2001 to Voudouris.

Figure 1A:
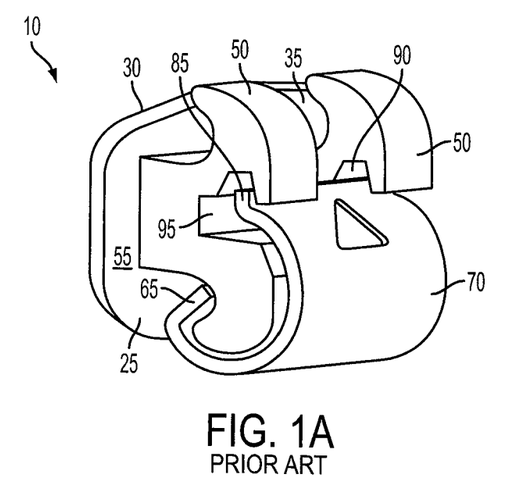
FIGS. 1A and 1B illustrate a prior art bracket.
Figure 1B:
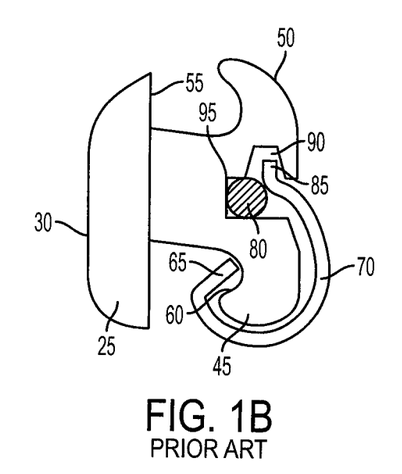
Figure 2A:
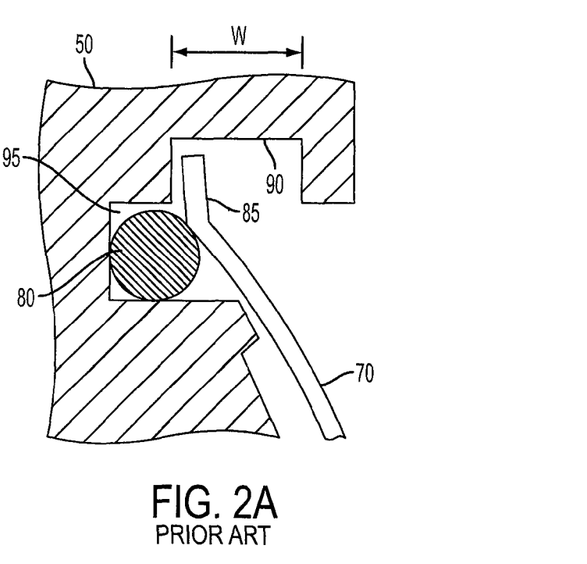
FIGS. 2A and 2B illustrate one problem with prior art brackets.
Figure 2B:
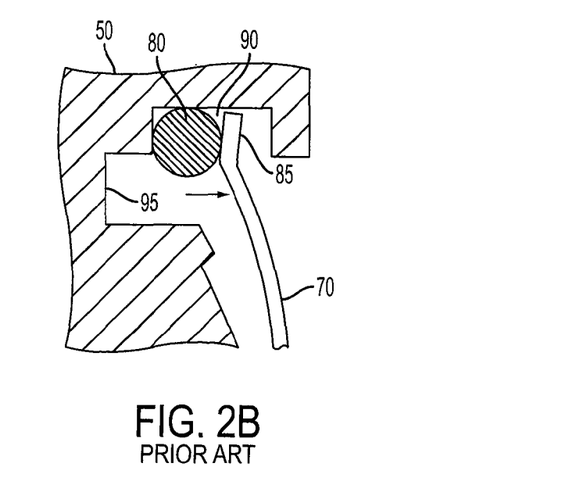

One such prior art bracket 10 is shown in FIGS. 1 and 2, and includes a body 25 having a bonding base 30 for attachment to a tooth. The body includes an occlusal-gingivally extending opening 35, a lingual vertical slot 40, a pair of laterally spaced gingival tie wings 50, and a pair of laterally spaced occlusal tie wings 45. The gingival 50 and occlusal tie wings 45 project from a labial surface 55 of the body 25, with the occlusal tie wings 45 defining one or more grooves 60 for receiving one or more arm members 65 of a locking shutter 70 through the occlusal tie wings 45. An archwire slot 95 is provided extending mesiodistally across the body 25 and between the gingival 50 and occlusal 45 tie wings at opposed mesial and distal sides of the body to accommodate an archwire 80. The locking shutter 70 is moveable between an open position in which placement and removal of the archwire is facilitated and a closed position in which placement and removal of the archwire is inhibited (as illustrated). In the closed position, a retaining portion 85 of the locking shutter 70 is friction fit into a retaining groove 90 formed adjacent to the archwire slot 95, in each of the gingival tie wings 50. During normal use, when the locking shutter 70 is in the closed position, as shown in FIG. 2A, the archwire 80 is pressed into, and seated entirely within the archwire slot 95. However, applicant has discovered that when an unexpected large external force is applied to the archwire 80, the archwire 80 can slip and enter the retaining groove 90, and become caught therein, as shown in FIG. 2B. FIGS. 2A and 2B are illustrated with the retaining groove 90 shown in exaggerated proportion for illustrative purposes.

In such a state, the archwire fails to shift smoothly inside the archwire slot where it belongs, resulting in a hindrance to and uneven tooth movement during the orthodontic treatment. To avoid such a state, it has been proposed to decrease the width W of the retaining groove, but if the width W is decreased, the functioning of the locking shutter, specifically with regards to its ability to press down wires ranging from the narrow round wires to full-size square wire, is impaired.

In addition, there has been a problem in that when an unexpectedly large external force is applied to the archwire, a tip portion of the locking shutter may become deformed as the archwire is twisted, thereby rendering the archwire retention unstable so as to pull out of the archwire slot. In the structure disclosed in U.S. Pat. No. 5,906,486, an arrangement is shown in which the position of the tip portion of the locking member is restricted in such a manner as to close both ends of the retaining groove. In such a structure, however, since the arrangement is provided so as to close both ends of the retaining groove, the width of the tip portion of the locking member must be inevitably made smaller than the length of the slot. Accordingly, there has been a drawback in that the tip portion of the locking member has insufficient rotational control since its length for holding the archwire is shortened. A second problem is that by making the locking shutter smaller, and therefore relatively weaker, there is less force to press against the archwire.

There is therefore a need in the art for an orthodontic bracket having improved archwire retention, and that addresses one or more of the aforementioned problems with the prior art.

SUMMARY OF THE INVENTION

According to one embodiment of the invention, there is provided an orthodontic bracket for attaching an archwire to a tooth including a body including a bonding base for attachment to the tooth, the body having an occlusal-gingivally extending opening, a lingual vertical slot, a pair of laterally spaced gingival tie wings and a pair of laterally spaced occlusal tie wings, the gingival and occlusal tie wings projecting from a labial surface of the body. An archwire slot is provided extending mesdiodistally across the body and between the gingival and occlusal tie wings at opposed medial and distal sides of the body to accommodate the archwire. A locking shutter including at least one resilient arm member at one end and a retaining portion at another end is provided such that the locking shutter moveable between an open position in which placement and removal of the archwire is facilitated and a closed position in which placement and removal of the archwire is inhibited. There is further provided a retaining groove formed in an occlusal wall of the gingival tie wings for releasably retaining a retaining portion of the locking shutter in the closed position and, a blocker for preventing movement of the archwire out of the archwire slot and into the retaining groove.

According to one aspect of the invention, the blocker is a blocking member on an outer surface of at least one of the gingival tie wings.

According to another aspect of the invention, the blocker a blocking member on an inner surface of at least one of the gingival tie wings.

According to another aspect of the invention, the blocking member is a rectangular block.

According to another aspect of the invention, the gingival tie wings include a tie wing body, a labially curved portion extending from the tie wing body and a blocking portion formed integrally with and extending mesiodontally away from the tie wing body; wherein the blocking portion forms means for preventing movement of the archwire out of the archwire slot and into the retaining groove.

According to another aspect of the invention, the blocking member includes an elongate edge aligned with a gingival edge of the gingival tie wings, and a shorter edge aligned with a front edge of the gingival tie wings.

According to another embodiment of the invention, there is there is provided an orthodontic bracket for attaching an archwire to a tooth including a body including a bonding base for attachment to the tooth, the body having an occlusal-gingivally extending opening, a lingual vertical slot, a pair of laterally spaced gingival tie wings and a pair of laterally spaced occlusal tie wings, the gingival and occlusal tie wings projecting from a labial surface of the body. An archwire slot is provided extending mesdiodistally across the body and between the gingival and occlusal tie wings at opposed medial and distal sides of the body to accommodate the archwire. A locking shutter including at least one resilient arm member at one end and a retaining portion at another end is provided such that the locking shutter moveable between an open position in which placement and removal of the archwire is facilitated and a closed position in which placement and removal of the archwire is inhibited. There is further provided a retaining groove formed in an occlusal wall of the gingival tie wings for releasably retaining a retaining portion of the locking shutter in the closed position and, a blocker for preventing movement of the archwire out of the archwire slot and into the retaining groove. Preferably, the blocker provides for an increased area of contact between the archwire and the bracket whereby the torque applied from the archwire onto the bracket is increased.

According to an aspect of this embodiment, the blocking member is formed integrally with the gingival tie wings.

According to another aspect of this embodiment, the blocking member includes a rectangular block-structure.

According to another aspect of this embodiment, the blocking member extends beyond an outer edge of the archwire slot, and is sized and otherwise dimensioned to enclose the retaining groove.

According to another aspect of this embodiment, the blocking member includes an elongate edge aligned with a gingival edge of the gingival tie wings, and a shorter edge aligned with a front edge of the gingival tie wings.

According to another embodiment of the invention, there is provided a method for preventing movement of an archwire out of an archwire slot and into a retaining groove of an orthodontic bracket, wherein the orthodontic bracket is one as herein described. The method includes blocking an end of the retaining groove to thereby prevent movement of the archwire from entering the retaining groove.

According to another embodiment of the invention, there is provided a method for increasing the torque and rotational control in the vertical and horizontal axes applied by an archwire onto an orthodontic bracket, wherein the orthodontic bracket is as herein described. The method includes extending an outer surface of the gingival tie wings to enclose the retaining groove and thereby provide an increased surface area on the gingival tie wings with which the archwire is in contact.

BRIEF DESCRIPTION OF THE DRAWINGS

The novel features which are believed to be characteristic of the present invention, as to its structure, organization, use and method of operation, together with further objectives and advantages thereof, will be better understood from the following drawings in which a presently preferred embodiment of the invention will now be illustrated by way of example. It is expressly understood, however, that the drawings are for the purpose of illustration and description only, and are not intended as a definition of the limits of the invention. In the accompanying drawings.

DETAILED DESCRIPTION

Figure 3A:
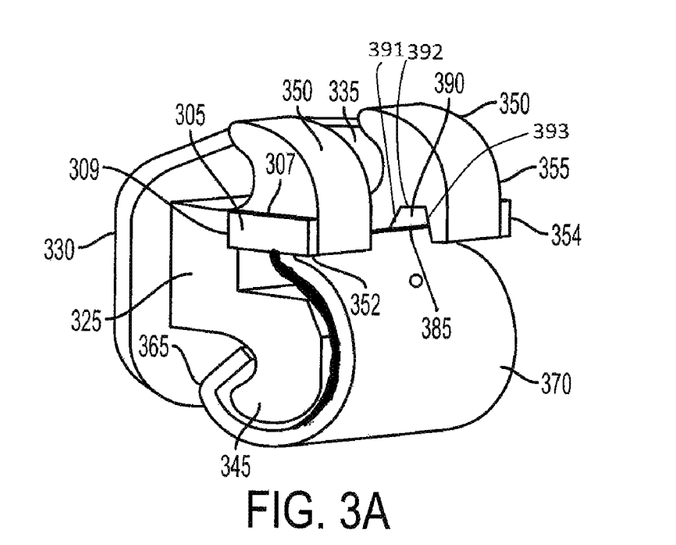
FIGS. 3A and 3B illustrate one embodiment of the orthodontic bracket according to the invention.
Figure 3B:
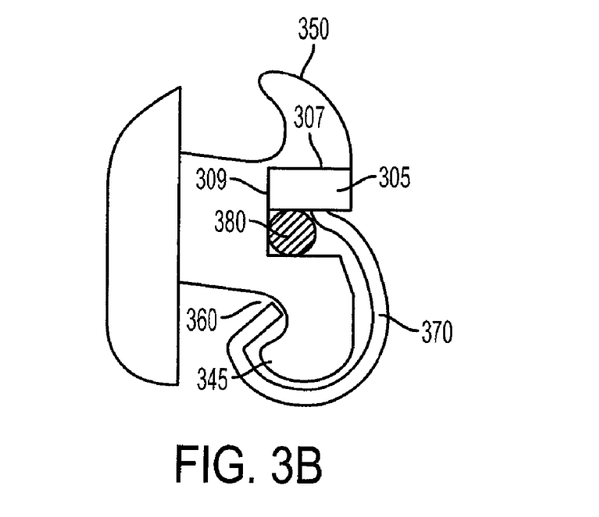
Figure 4A:
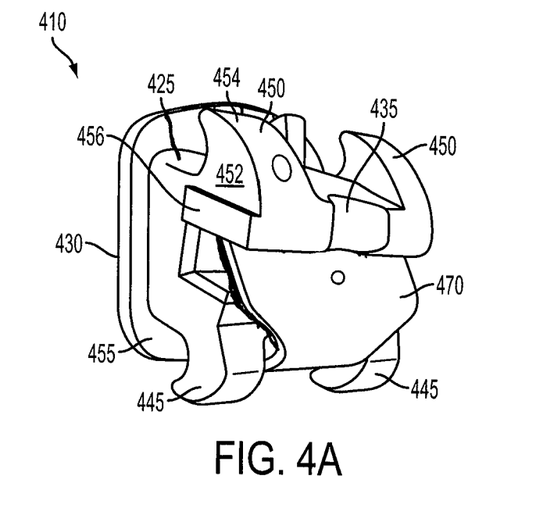
FIGS. 4A, 4B, 4C and 4D illustrate another embodiment of the orthodontic bracket according to the invention.
Figure 4B:
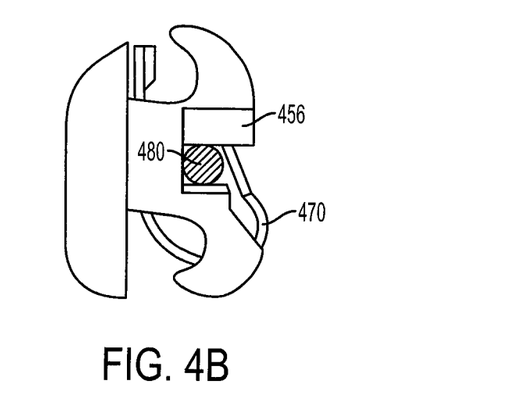
Figure 4C:
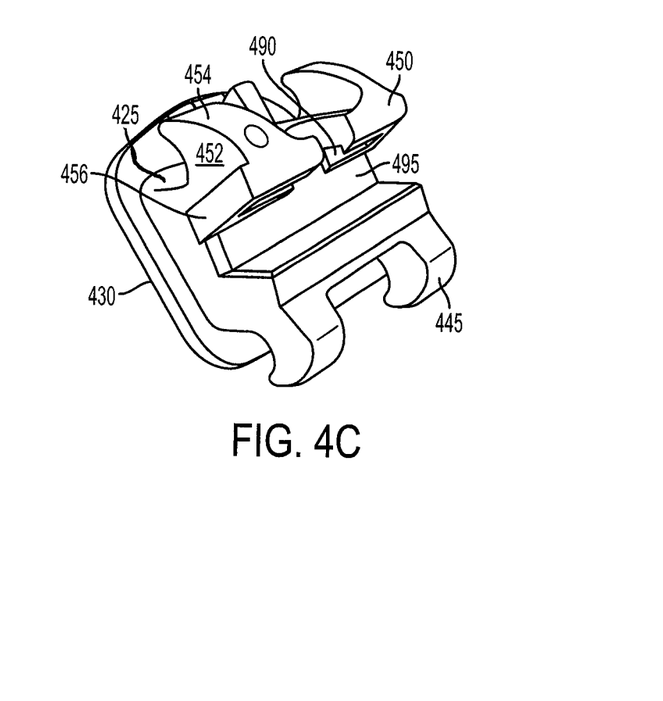
Figure 4D:
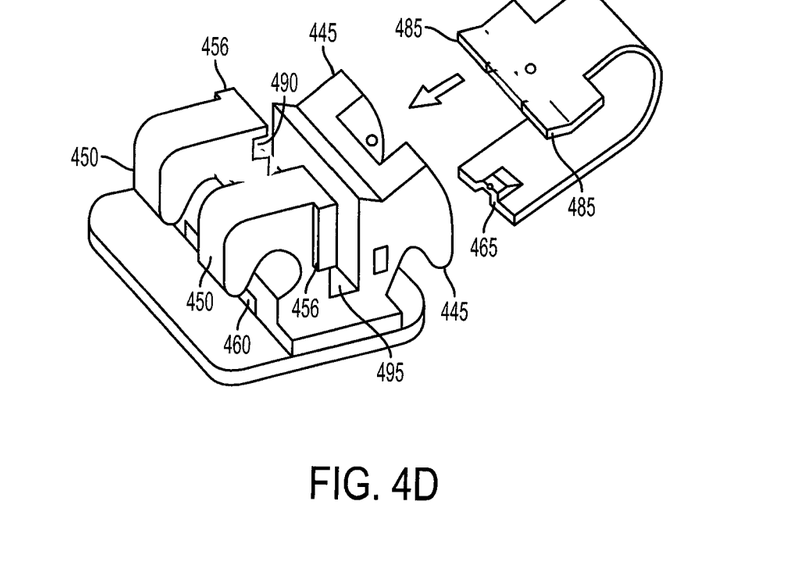

Referring now to FIGS. 3A-3B, there is shown one embodiment of the invention in which an orthodontic bracket 310 is illustrated as including a body 325 having a bonding base 330 for attachment to a tooth (not shown). The body 325 preferably includes an occlusal-gingivally extending opening 335 that is lingual to an archwire, a pair of laterally spaced gingival tie wings 350, and a pair of laterally placed occlusal tie wings 345. The gingival 350 and occlusal 345 tie wings project from a labial surface 355 of the body 325, with the occlusal tie wings 345 defining a groove 360 for receiving arm member 365 of a locking shutter 370 through the occlusal tie wings 345. An archwire slot 395 is provided extending mesiodistally across the body 325 and between the gingival 350 and occlusal 345 tie wings at opposed mesial and distal sides of the body 325 to accommodate an archwire 380. The locking shutter 370 is moveable between an open position in which placement and removal of the archwire is facilitated and a closed position in which placement and removal of the archwire is inhibited (as illustrated). In the closed position, a retaining portion 385 of the locking shutter 370 is compression fit (or otherwise) into a retaining groove 390 formed of lingual wall 391, gingival wall 392 and labial wall 393 and located adjacent to the archwire slot 395, in each of the gingival tie wings 350. In some variations of the invention, the arm member 365 of the locking shutter 370 is made up of two arm members, such that only portions of the arm members sized and otherwise dimensioned to be in contact with the groove 360 of the occlusal tie wings 345 are present. Various modifications to the arm member may be made without departing from the invention, wherein it is understood that the design and shape of the arm member is to facilitate the locking and opening of the locking shutter in a friction fit, compression fit, or snap fit arrangement.

It will be understood that the terms occlusal tie wings and gingival tie wings may be readily interchanged with each other depending upon the relative positioning of the bracket on the patient's tooth. That is, when the bracket is placed on the bottom of a user's mouth, the gingival tie wings are those located on the bottom of the bracket closest to the gums, and when the bracket is placed on the top of a user's mouth, the gingival tie wings are those located on the top of the bracket closest to the gums. The orthodontic bracket as herein described could thus have those elements and features described with respect to the gingival tie wings appear on the occlusal tie wings, and vice versa.

While the locking shutter 370 functions to lock the archwire 380 generally within the bracket, and particularly within the retraining groove 390, under disproportionate loading situations, the tension in the archwire 380 may be sufficiently high to cause the locking shutter 370 to be displaced slightly, and thus allow the archwire 380 to slip into the retaining groove 390. Accordingly, the invention provides a means for preventing movement of the archwire 380 out of the archwire slot 395 and into the retaining groove 390. In the embodiment of FIGS. 3A and 3B, the means for preventing includes a blocking member 305 rigidly connected to one or both of the respective outer surfaces 355 of the gingival tie wings 350. The blocking member 305 may be connected to the outer surfaces 355 by welding, or alternatively, may be provided with a threaded fastener (not shown) that engages a thread on the gingival tie wing 350. With this arrangement, the blocking member 305 may be retrofitted onto existing orthodontic brackets, or otherwise added on and/or removed depending on whether it is required given a particular size and shape of archwire 380.

As illustrated, blocking member 305 is preferably a generally rectangular-block shaped member having an elongate edge 307 aligned with an occlusal edge 352 of the gingival tie wings 350, and a shorter edge 309 aligned with a front or labial edge 354 of the gingival tie wings 350. In a preferred embodiment, the edges of the blocking member 305 extend mesial or distal from the gingival tie wings 350 and are rounded, chamfered, or otherwise smoothed to avoid any sharp edges associated with the orthodontic bracket. Accordingly, it will be appreciated by a person skilled in the art that the archwire 380 is now altogether prevented from entering the retaining groove 390, as any tension on the archwire in a direction towards the retaining groove 390 will be restrained by the portion of the blocking member 305 proximate the retaining groove 390. An additional surprising benefit of this arrangement is that the archwire 380 is supported at a further distance away from a centre point of the archwire slot 395 within the bracket, therefore resulting in a higher moment and torque for more effective movement being applied onto the orthodontic bracket, and improving efficacy of the orthodontic tooth leveling, derotation and torque control. In addition, the broader, wider distance away from the centre of the locking shutter prevents a sharp bend in the archwire to prevent notching or bonding of the archwire during early tooth movement and sliding of teeth during mid-term treatment tooth movement.

Figure 6A:
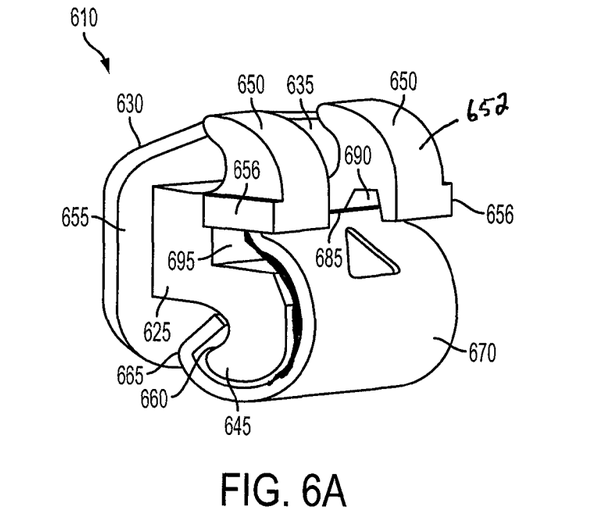
FIGS. 6A and 6B illustrate another embodiment of the orthodontic bracket according to the invention.
Figure 6B:
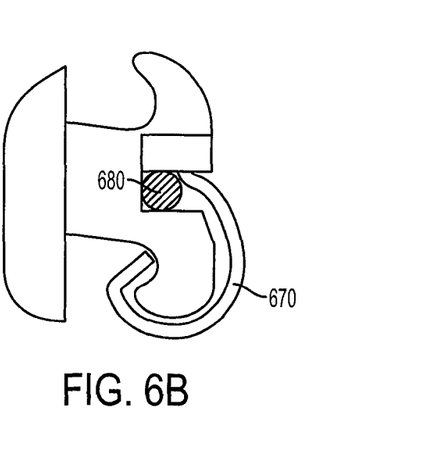
Figure 7A:
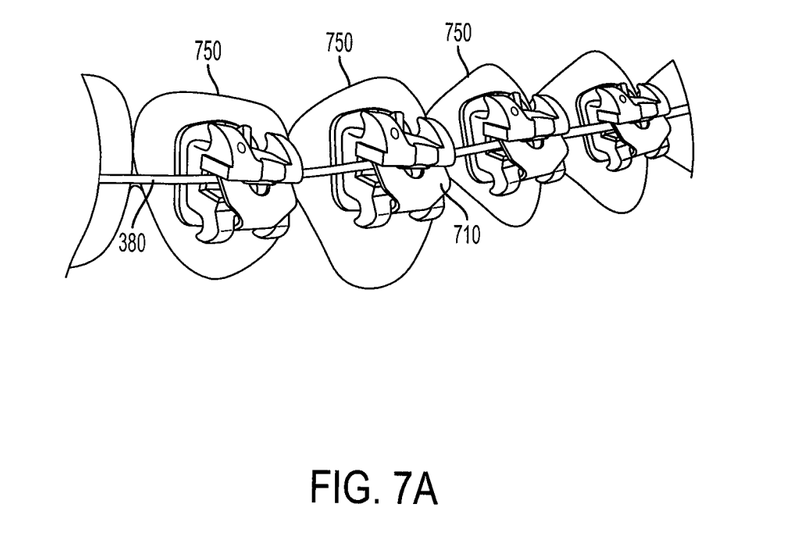
FIGS. 7A and 7B illustrate embodiments of the orthodontic bracket according to the invention during treatment.
Figure 7B:
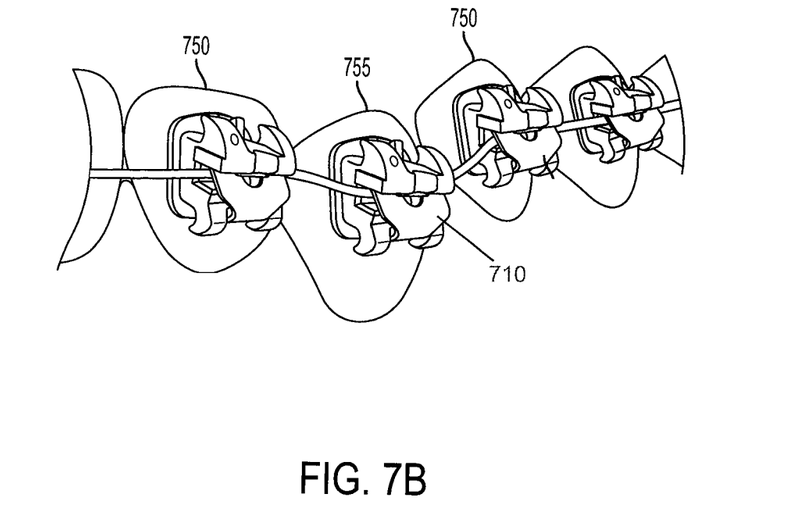

Referring now to FIGS. 6 and 7, there is shown the orthodontic bracket according to the invention, during treatment. In FIG. 6, the archwire 380 generally follows a consistent curvature around the teeth and does not experience any sudden shifts or changes in direction. This would be the case where treatment is required for teeth being offset rotationally or labially. In FIG. 7, one tooth 755 rests lower than the adjacent teeth 750 in a gingival direction. To accommodate this, while still providing effective orthodontic treatment, the orthodontic bracket 710 rests lower than the brackets 650, and accordingly, the archwire 380 dips into an approximate "U" shape. By providing the blocking member 305 as herein described, the bottom portion of the "U" is made longer resulting in a larger portion of the archwire 380 on which forces from the orthodontic bracket 710 would act, and accordingly a lower pressure being applied on the archwire over the region at which the archwire 380 dips into the approximate "U" shape and is in contact with portions of the orthodontic bracket. This results in less wear on the archwire 310 during treatment periods, and also reduces the possibility of damage, wear or deformation such as wire notching that would bind the bracket against the notched archwire resisting tooth movement when the orthodontic device is being applied to a patient by an orthodontist.

Referring now to FIGS. 4A-4D, there is shown another embodiment of the invention in which an orthodontic bracket 410 is illustrated as including a body 425 having a bonding base 430 for attachment to a tooth (not shown). The body 425 preferably includes an occlusal-gingivally extending opening 435 located lingual to an archwire slot, a pair of laterally spaced gingival tie wings 450, and a pair of laterally placed occlusal tie wings 445. The gingival 450 and occlusal 445 tie wings project from a labial surface 455 of the body 425. An archwire slot 495 (shown in FIG. 4C) is provided extending mesiodistally across the body 425 and between the gingival 450 and occlusal 445 tie wings at opposed mesial and distal sides of the body 425 to accommodate an archwire 480. A locking shutter 470 is moveable between an open position in which placement and removal of the archwire is facilitated and a closed position in which placement and removal of the archwire is inhibited (as illustrated). In the closed position, retaining portions 485 of the locking shutter 470 are compression fit (or otherwise) into a retaining groove 490 formed adjacent to the archwire slot 495, in each of the gingival tie wings 450. Arm member 465 of the locking shutter 470 is sized and otherwise dimensioned to be in contact with a lock portion 460 in the bracket body. Various modifications to the arm member may be made without departing from the invention, wherein it is understood that the design and shape of the arm member is to facilitate the locking and opening of the locking shutter in a friction fit, compression fit, or snap fit arrangement. The locking shutter may thus be made solid to provide a greater compression fit into the retaining groove, as shown in the Figures.

In this embodiment, the gingival tie wings 450 are sized, shaped and otherwise dimensioned to themselves provide for a means for preventing the archwire 480 from moving out of the archwire slot 495 and into the retaining groove 490. The novel gingival tie wings 450 according to the invention preferably include a tie wing body 452 extending from the body 425 of the orthodontic bracket, in a direction away from the tooth, and a labially curved portion 454 extends from the tie wing body 452. A retaining groove 490 in the tie wing body 452 is formed adjacent to the archwire slot 495 of the body 425. There is further provided a blocking portion 456 formed integrally with, and extending mesiodontally away from the tie wing body 452. The blocking portion 456 extends beyond a surface of the gingival tie wing 450 at which the retaining groove 490 ends, such that the retaining groove 490 extends through the body 425 of the orthodontic bracket, but does not extend through the external blocking portion 456 of the gingival tie wing 450.

Figure 5A:
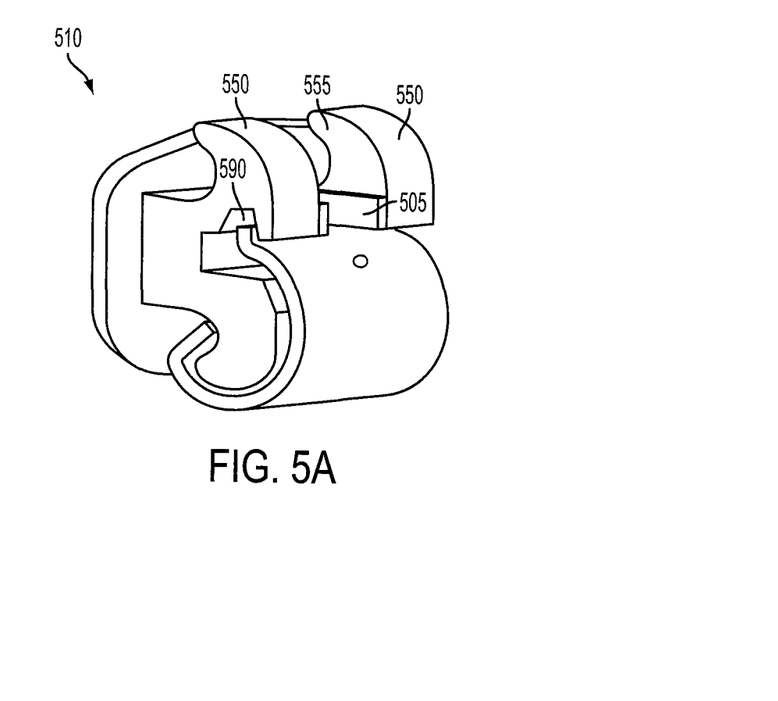
FIGS. 5A and 5B illustrate another embodiment of the orthodontic bracket according to the invention.
Figure 5B:
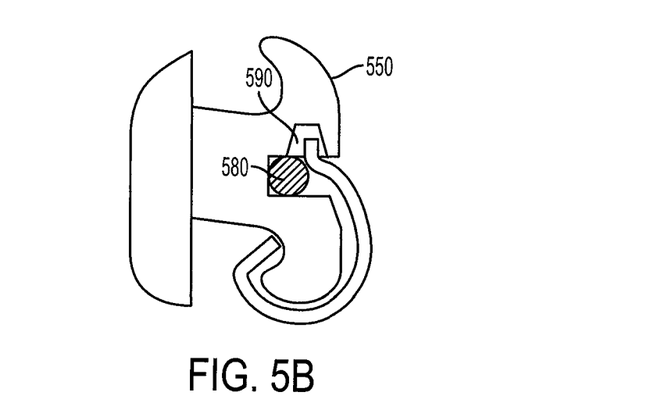

Referring now to FIGS. 5A and 5B, there is shown another embodiment of the invention, wherein the means for preventing movement of the archwire from the archwire slot into the retaining groove includes a blocking member 505 provided on one or both of the inner surfaces 555 of the gingival tie wings 550. The blocking member 505 is preferably formed of a corresponding shape and size as the blocking member 305 described with respect to FIGS. 3A and 3B. The benefit provided by providing blocking member 505 on the internal surfaces 555 of the gingival tie wings 550 is that the blocking member 505 is positioned entirely within a protected area of the orthodontic bracket 510, such that a patient's tongue will not feel any difference in the orthodontic bracket 510 during a treatment period. In any event, as will be evident from the figures and the description, the blocking member 505 on the internal surfaces 555 of one or both of the gingival tie wings 550 prevents the archwire 580 from entering the retaining groove 590.

In another embodiment of the invention, as shown in FIGS. 6A and 6B, there is provided an orthodontic bracket 610 having a body 625 with a bonding base 630 for attachment to a tooth (not shown). The body 625 preferably includes an occlusal-gingivally extending opening 635, a pair of laterally spaced gingival tie wings 650, and a pair of laterally placed occlusal tie wings 645. The gingival 650 and occlusal 645 tie wings project from a labial surface 655 of the body 625, with the occlusal tie wings 645 defining a groove 660 for receiving arm member 665 of a locking shutter 670 through the occlusal tie wings 645. An archwire slot 695 is provided extending mesiodistally across the body 625 and between the gingival 650 and occlusal 645 tie wings at opposed mesial and distal sides of the body 625 to accommodate an archwire 680. The locking shutter 670 is moveable between an open position in which placement and removal of the archwire is facilitated and a closed position in which placement and removal of the archwire is inhibited (as illustrated). In the closed position, a retaining portion 685 of the locking shutter 670 is compression fit into a retaining groove 690 formed adjacent to the archwire slot 695, in each of the gingival tie wings 650.

In this embodiment, the gingival tie wings 650 are sized, shaped and otherwise dimensioned to themselves provide for a means for preventing the archwire 680 from moving out of the archwire slot 695 and into the retaining groove 690. The novel gingival tie wings 650 according to the invention preferably include a tie wing body 652 extending from the body 625 of the orthodontic bracket, in a direction away from the tooth, and a labially curved portion 654 extends from the tie wing body 652. A retaining groove 690 in the tie wing body 652 is formed adjacent to the archwire slot 695 of the body 625. There is further provided a blocking portion 656 formed integrally with, and extending mesiodontally away from the tie wing body 652. The blocking portion 656 extends beyond a surface of the gingival tie wing 650 at which the retaining groove 690 ends, such that the retaining groove 690 extends through the body 625 of the orthodontic bracket, but does not extend through the blocking portion 656 of the gingival tie wing 650. With this arrangement, a full width of the locking shutter 670 as is provided in the prior art may still be used, and no modifications would be required to the locking shutter 670, as illustrated. Preferably, the edges of the gingival tie wings 550 according to this embodiment are rounded, or otherwise smoothed.

It will be appreciated by those skilled in the art that the invention described herein may be applied to variations on the orthodontic brackets generally illustrated in the figures and described herein. In particular, however, the invention is chiefly applicable to orthodontic brackets of the type known in the art as "siamese twin brackets" that include the vertical space described above between each of the tie wings. Brackets of this type (as opposed to mono-block or single brackets) are prone to the problem as herein discussed, and accordingly, the invention solves the problem as associated with these siamese twin brackets. Mono-block or single brackets do not have the tie wings as herein described, and accordingly have a longer surface of contact within the retaining groove, thereby permitting easier modifications to be made to the locking shutter. As is known in the art, however, mono-block or single brackets suffer from other deficiencies in orthodontic treatment such as derotation of teeth. Accordingly, and based on the general shape of these mono-block brackets, the invention is generally not applicable to these types of brackets and particularly to the embodiments having the internal blocking member.

As described earlier, one other advantage of certain embodiments of the invention as herein described, aside from preventing movement of the archwire out of the archwire slot and into the retaining groove for retaining the locking shutter is the provision of an increased contact surface area between the archwire and the combination of the archwire slot and the blocking member (or the blocking portion of the gingival tie wings in some embodiments). This increased contact surface area and longer line of contact between the archwire and the orthodontic bracket itself results in a higher moment arm than prior art siamese twin-type brackets, and accordingly, a more effective orthodontic treatment can be provided as higher forces can be placed on the tooth with relatively less tension in the archwire itself, or alternatively, a thinner archwire being used. In addition, the broader locking shutter prevents a sharp bend in the archwire to prevent notching or bonding of the archwire during early tooth movement and sliding of teeth during mid-term treatment tooth movement.

Figure 8:
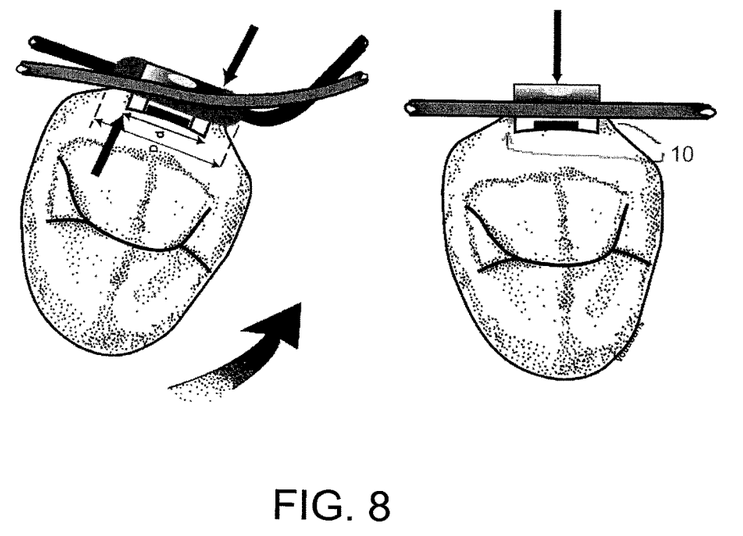
FIG. 8 illustrates the improved rotational control resulting from the invention.

Furthermore, the orthodontic bracket as herein described provides for increased vertical rotational forces about an axis in a plane parallel to the front surface of the tooth. The increase in vertical rotational forces aids in the orthodontic effect of the bracket 710 with respect to adjusting the angle of each teeth on which the bracket 710 is positioned. Furthermore, in embodiments where the blocking member is positioned on the external surface of the gingival tie wings, or is formed integrally with the gingival tie wings, the blocking member aids in the vertical leveling ability and vertical rotation control (as shown in FIG. 8) by providing an increased distance between the points of contact of the archwire wire 380 with the blocking members. An analogous advantage becomes available due to increased horizontal rotational forces.

Examples of the other siamese twin brackets having the vertical space between the gingival tie wings, materials used therein and other details of constructions to which the invention may be applied are described in U.S. Pat. No. 6,368,105 issued Apr. 9, 2002 to Voudouris et al., and in U.S. Pat. No. 6,168,428 to Voudouris issued Jan. 2, 2001, the contents of each of these are herein expressly incorporated by reference.

For clarity, applicant provides the following definitions for terms used throughout the description and claims. References to a "locking shutter" refer to the portion of the orthodontic bracket that is capable of shutting, closing, making secure, or preventing displacement of the archwire. References to a "retaining groove" refer to an indentation or small hollow that permits engagement by a portion of the locking shutter to fix the locking shutter in place.

The invention claimed is:

1. An orthodontic bracket for attaching an archwire to a tooth comprising:
   a body including a base for attachment to the tooth, a lingual lock portion, a mesial gingival tie wing, a distal gingival tie wing, and at least one occlusal tie wing, said gingival and occlusal tie wings projecting from a labial surface of said body;
   an archwire slot extending mesiodistally across said body and between the gingival and occlusal tie wings at opposed mesial and distal sides of said body to accommodate the archwire;
   a locking shutter including at least one resilient arm member and a retaining portion, said locking shutter moveable between an open position in which placement and removal of said archwire is facilitated and a closed position in which placement and removal of said archwire is inhibited;
   a retaining groove:
   formed in an occlusal wall of each of said gingival tie wings;
   having a gingival wall, a labial wall, and a lingual wall;
   having a width such that said locking shutter can press down said archwire when retained therein; and
   extending mesiodistally through the body, for releasably retaining said retaining portion of said locking shutter in said closed position; and
   a mesial blocking member projecting mesiodistally off from a mesial surface of said mesial gingival tie wing outwardly from said bracket, and a distal blocking member projecting mesiodistally off from a distal surface of said distal gingival tie wing outwardly from said bracket, the mesial and distal blocking members extending labial-lingually across respective mesial and distal ends of said retaining groove for preventing movement of said archwire out of said archwire slot and into said retaining groove in said closed position when tension in said archwire causes said locking shutter to be displaced thus allowing said archwire to slip out of said archwire slot and into said retaining groove;
   wherein said resilient arm member is sized and dimensioned to be in contact with said lingual lock portion; and
   wherein said mesial and distal blocking members each comprises: an elongate edge aligned with an occlusal edge of the corresponding gingival tie wing: and a shorter edge aligned with a labial edge of the corresponding gingival tie wing.

2. An orthodontic bracket according to claim 1, wherein said mesial blocking member is integrally formed with said mesial gingival tie wing, and wherein said distal blocking member is integrally formed with said distal gingival tie wing.

3. An orthodontic bracket according to claim 1, wherein said mesial and distal blocking members each comprises a rectangular block.

4. An orthodontic bracket according to claim 1, wherein said retaining portion is one of: compression fit, snap fit, and friction fit into said retaining groove in said closed position.

5. The orthodontic bracket according to claim 1, wherein each of said mesial and distal blocking members is removable.

6. The orthodontic bracket according to claim 1, wherein said elongated and shorter edges are each one of: rounded, chamfered, and smoothed.

\* \* \* \* \*